(12) United States Patent
Rand et al.

(10) Patent No.: US 6,568,389 B1
(45) Date of Patent: May 27, 2003

(54) INHALATION DEVICE

(75) Inventors: Paul Kenneth Rand, Ware (GB); Gregor John McLennan Anderson, Ware (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/806,043

(22) PCT Filed: Sep. 23, 1999

(86) PCT No.: PCT/EP99/07080

§ 371 (c)(1),
(2), (4) Date: May 11, 2001

(87) PCT Pub. No.: WO00/18458

PCT Pub. Date: Apr. 6, 2000

(30) Foreign Application Priority Data

Sep. 26, 1998 (GB) ............................................ 9820938

(51) Int. Cl.[7] ............................................... B65D 83/06
(52) U.S. Cl. ................................................. 128/203.15
(58) Field of Search ....................... 128/203.12, 203.15

(56) References Cited

U.S. PATENT DOCUMENTS

| | | |
|---|---|---|
| 3,622,053 A | 11/1971 | Ryden |
| 4,114,811 A | 9/1978 | Loeffler |
| 4,130,116 A | 12/1978 | Cavazza |
| 5,082,148 A | 1/1992 | Dunning |
| 5,284,133 A | 2/1994 | Burns et al. |
| 5,347,998 A | 9/1994 | Hodson et al. |
| 5,447,151 A | 9/1995 | Bruna et al. |
| 6,158,431 A | 12/2000 | Poole |
| 6,182,655 B1 | 2/2001 | Keller et al. |
| 6,223,746 B1 | 5/2001 | Jewett et al. |
| 6,260,549 B1 | 7/2001 | Sosiak |

FOREIGN PATENT DOCUMENTS

| | | | |
|---|---|---|---|
| DE | 3639836 A | 6/1988 | |
| EP | 0028929 A | 5/1981 | |
| GB | 2074454 A | * 4/1980 | .......... A61M/15/00 |
| GB | 2063075 | 6/1981 | |
| WO | WO9211051 A | 7/1992 | |
| WO | 9940959 | 8/1999 | |

* cited by examiner

Primary Examiner—William C. Doerrler
Assistant Examiner—Malik N. Drake
(74) Attorney, Agent, or Firm—James F. Risk

(57) ABSTRACT

There is provided an inhalation device suitable for dispensing medicament, particularly medicament for use in the treatment of respiratory disorders. The device comprises a body; a medicament carrier, locatable within said body; a mouthpiece, reversibly movable from a storage position wherein said mouthpiece is within the body to an in-use position wherein a portion of the mouthpiece protrudes from the body and wherein the mouthpiece is in communication with the medicament carrier to allow passage of medicament therebetween; and a mouthpiece actuator coupled to the mouthpiece such that actuation of the mouthpiece actuator moves the mouthpiece towards said storage position and deactuation of the mouthpiece actuator moves the mouthpiece towards the in-use position. The body is shaped to be holdable in one hand and the mouthpiece actuator is actuable in response to a motion of the thumb on the same hand.

21 Claims, 9 Drawing Sheets

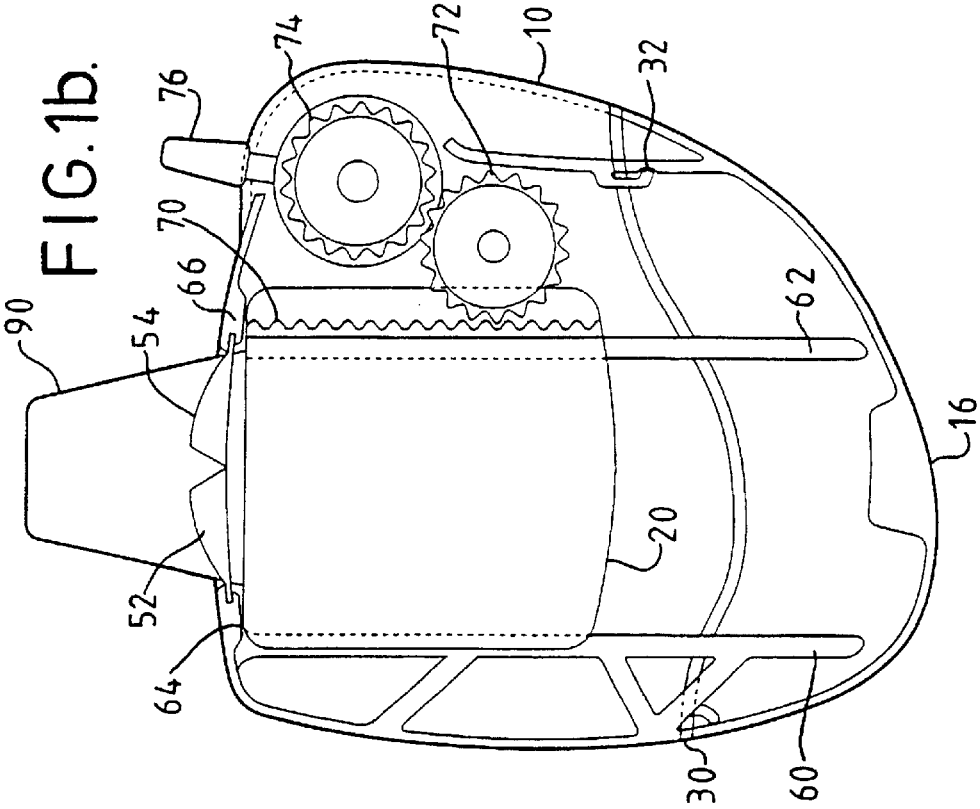
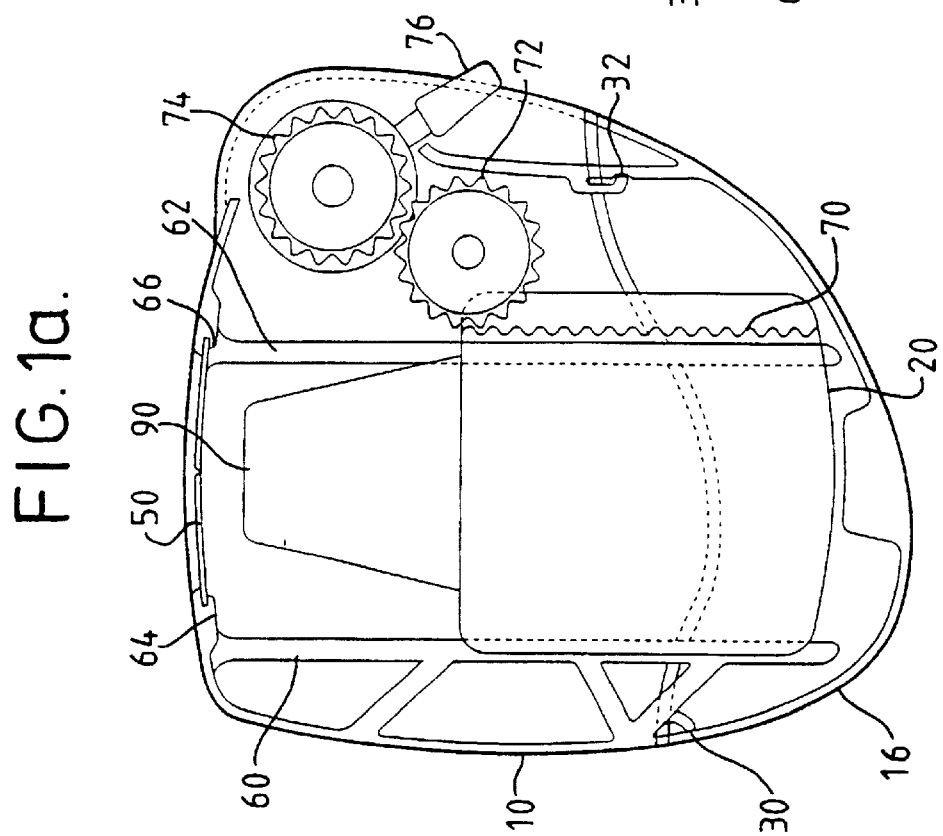

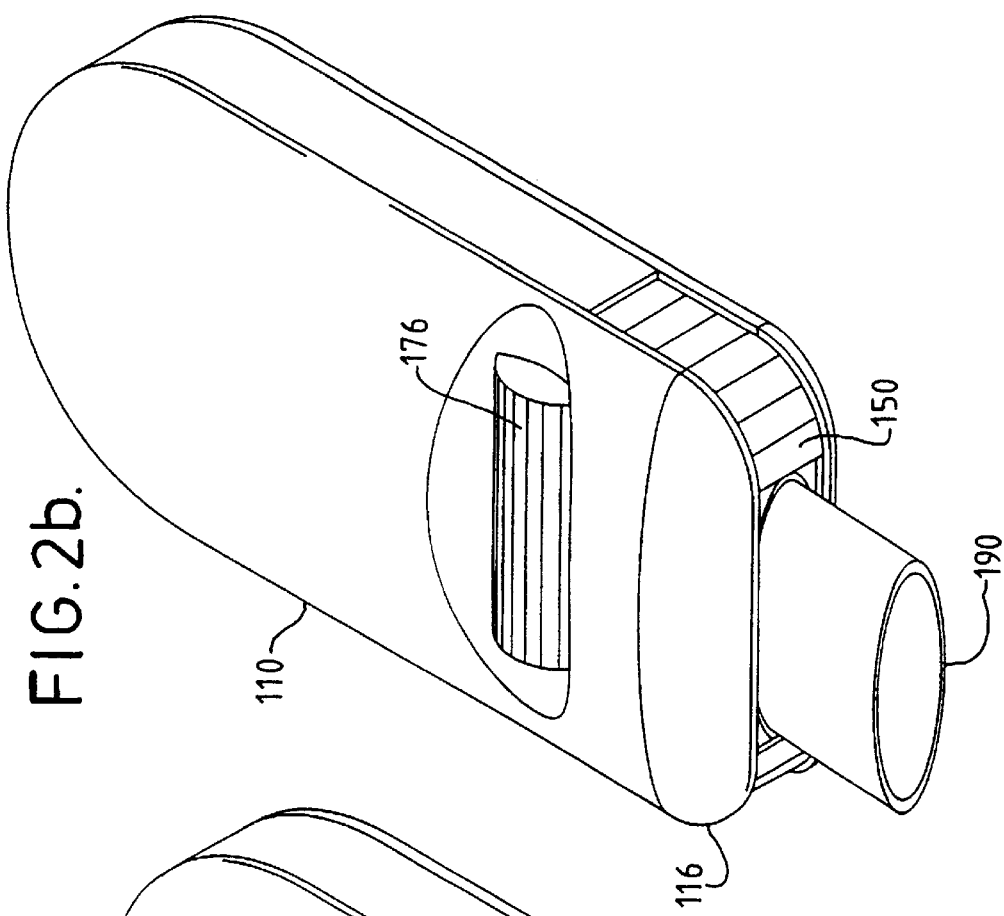
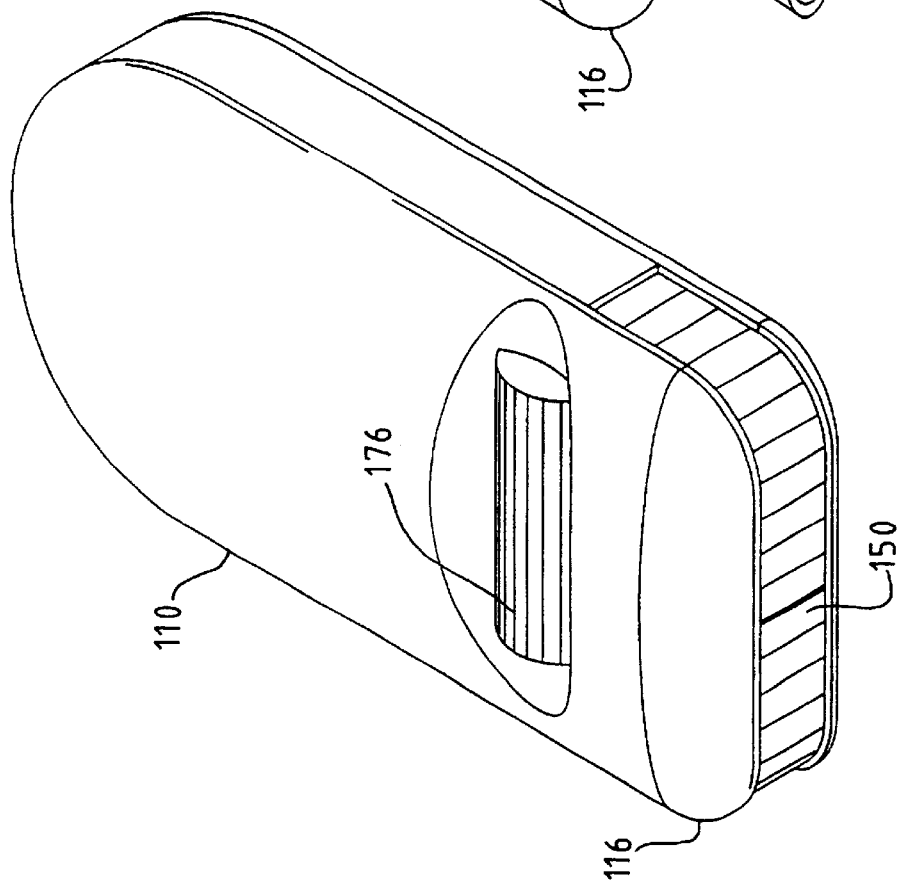

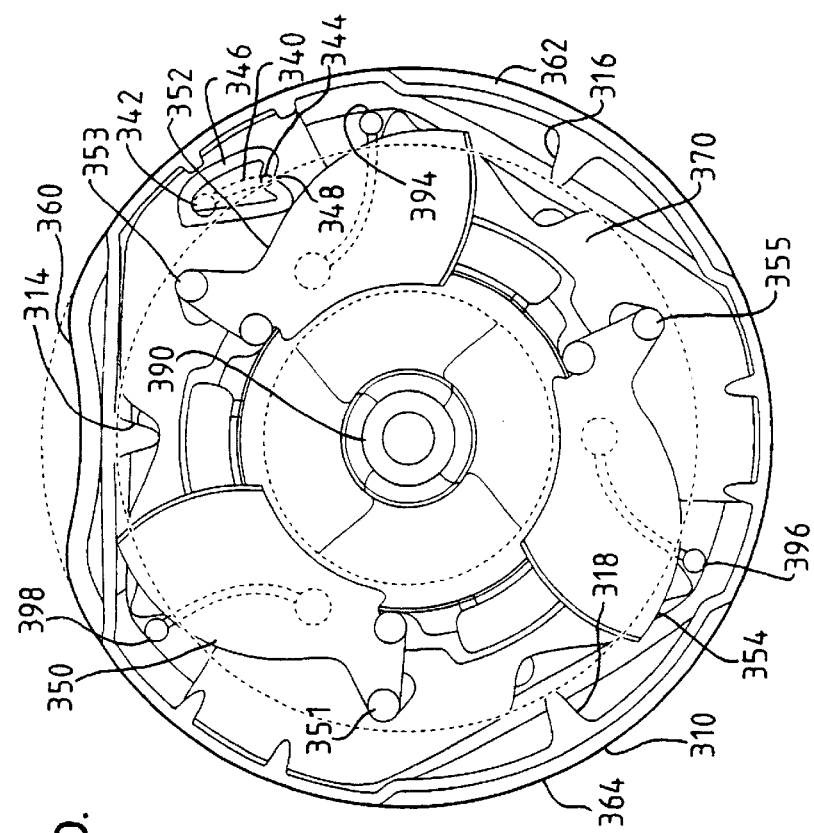
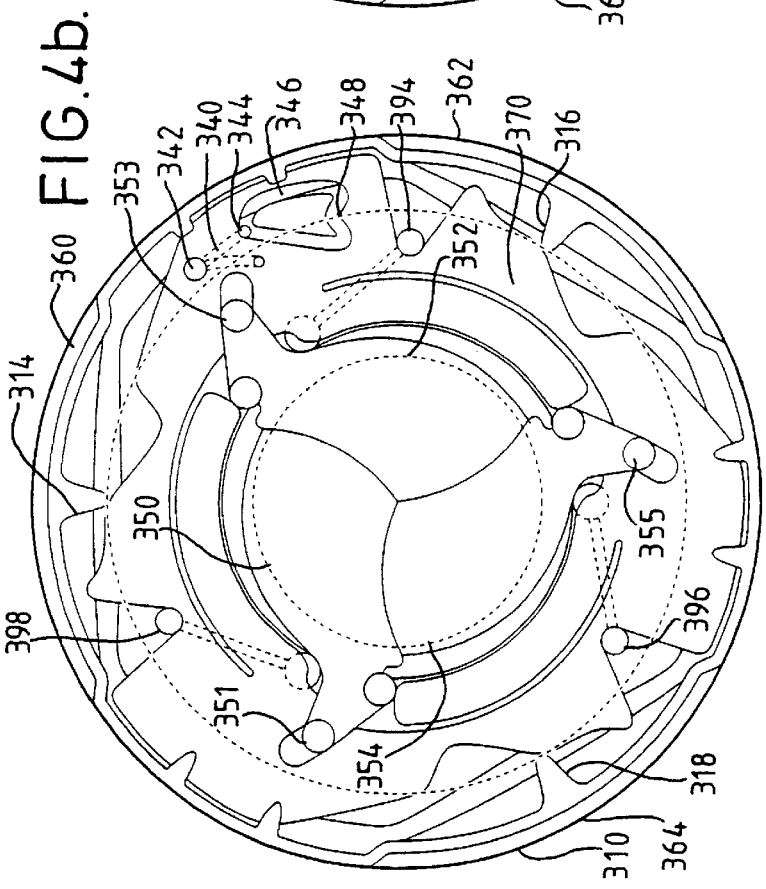
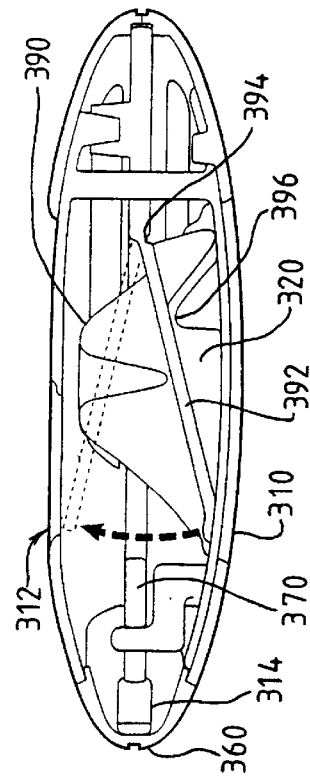
FIG.4c.
FIG.4b.
FIG.4a.

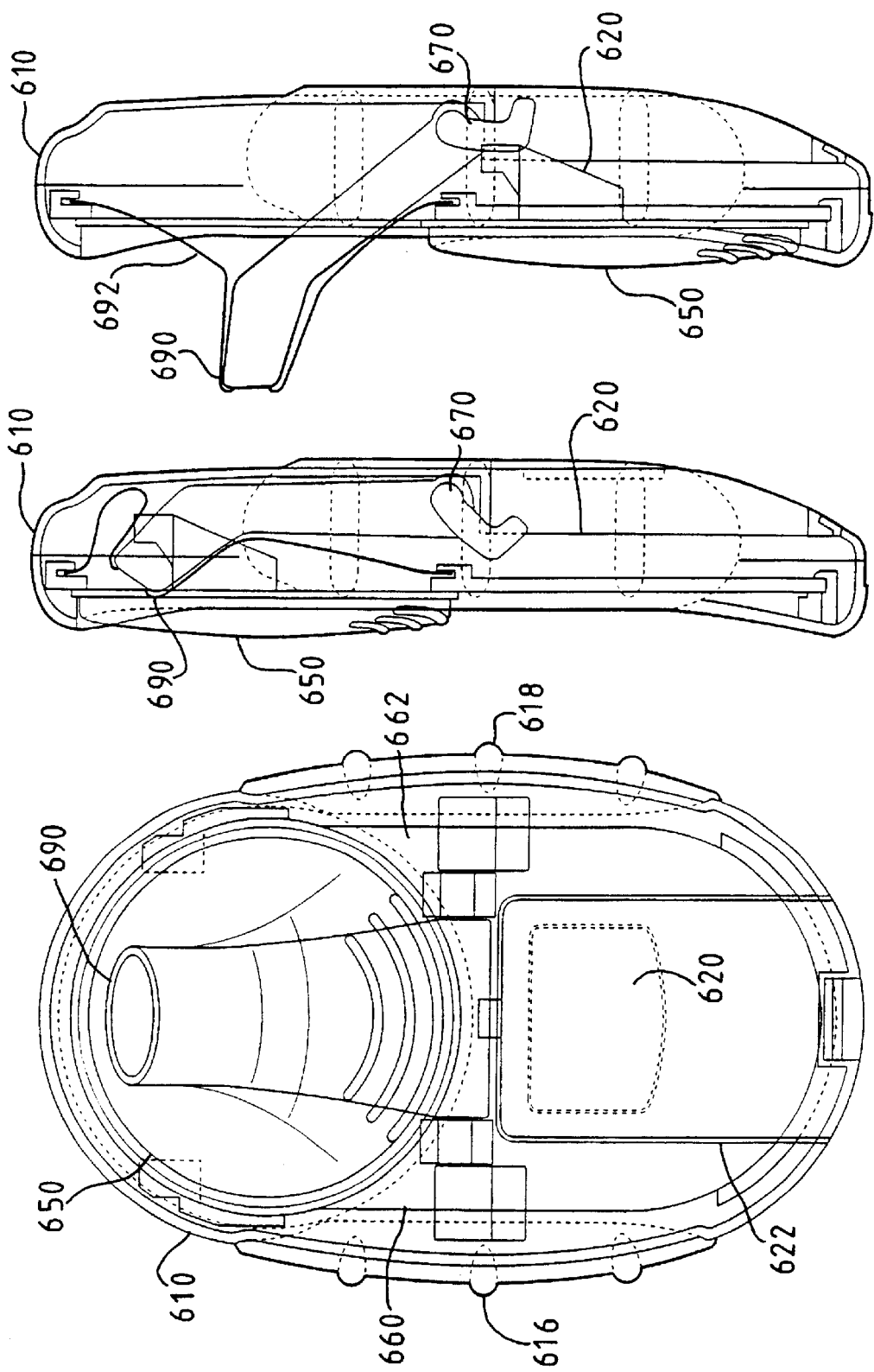

INHALATION DEVICE

This application is filed pursuant to 35 U.S.C. §371 as a U.S. National Phase Application of International Application No. PCT/EP99/07080 filed Sep. 23, 1999, which claims priority from GB9820938.0 filed Sep. 26, 1998 in the United Kingdom.

The present invention relates to an inhalation device for use in the administration of medicament to a patient. The device has a mouthpiece, which is reversibly retractable from a storage position located inside the body of the device to a dispensing position in which the mouthpiece protrudes from the body of the device.

The use of inhalation devices in the administration of medicaments, for example in bronchodilation therapy, is well known. Such devices generally comprise a body or housing within which a medicament container is located. A mouthpiece (or nozzle) is typically provided, wherein 'in use' the mouthpiece communicates with the medicament container to allow passage of medicament from the source to the mouthpiece and thence, to the patient.

In a typical dispensing operation the body of the device is held by the patient and the mouthpiece (or nozzle) of the inhalation device is placed in the mouth (or nose) of the patient. The patient inhales, thereby causing transfer of medicament from the medicament container to the interior of the body of the patient.

When not in use it is desirable, from a hygiene standpoint, that the mouthpiece is provided with some kind of protective cover. The cover desirably acts both to prevent build-up of dirt on the mouthpiece and to prevent ingress of dirt into the body of the device through the mouthpiece, which might then be subject to inhalation by a patient.

It is known to provide the mouthpiece with a protective cap which acts as a protective cover. The cap may either be an entirely separate element or it may be joined to the body of the device in some way. DE-A-3,639,836, for example, describes a device in which the protective cap is mounted on an arm, which is pivotally mounted to the body of the device.

As an alternative to the use of a protective cap, one might envisage a device having a mouthpiece which is reversibly retractable from a storage position in which the mouthpiece is contained within the body of the device to a dispensing position in which the mouthpiece protrudes from the body of the device. In a device of this type the body of the device itself acts as the protective cover when the mouthpiece is in the storage position. The mouthpiece cover is thus an integral part of the inhalation device, avoiding contamination problems of prior art inhalation devices caused by the loss of removable mouthpiece covers.

GB-A-2,074,454 describes an inhalation device comprising a tubular body adapted for detachable fitting to an aerosol container. A mouthpiece is provided, which is movable from a storage position to a dispensing position by means of a cap, rotatably mounted on the tubular body, which has actuating means associated therewith. The cap and tubular body are provided with openings of similar dimensions. Manual rotation of the cap to bring the openings into register causes the actuating means to move the mouthpiece to the dispensing position in which the mouthpiece protrudes from the body of the device. Conversely, rotation of the cap by the user to bring the openings out of register causes the mouthpiece to be moved to the storage position in which the mouthpiece is contained within the body of the device.

For the convenience of the user, it is desirable that the inhalation device is arranged to allow movement of the mouthpiece from the storage to dispensing position (and vice-versa) by a one-handed operation. The device described in GB-A-2,074,454 would be very difficult to operate by means of a one-handed operation since it requires a rotatory movement of the cap relative to the body. This would normally require the user to hold the body in one hand, the cap in another and thence, to perform the required relative rotatory movement.

The Applicants have now found that the desired one-handed operation can be facilitated where the device is shaped for ease of grip by the palm and fingers of one hand and where the mouthpiece is actuable by a motion of the thumb of the same hand. One handed operation is thus, for example, achievable if the user holds the body of the device in the palm of a partially cupped hand and employs the thumb to provide movement to the mouthpiece actuator, thereby causing actuation of the mouthpiece.

According to one aspect of the present invention there is provided an inhalation device for dispensing medicament comprising
  a body;
  a medicament carrier;
  a mouthpiece, reversibly movable from a storage position wherein said mouthpiece is within said body to an in-use position wherein a portion of the mouthpiece protrudes from the body and wherein the mouthpiece is in communication with said medicament carrier to allow passage of medicament therebetween; and
  a mouthpiece actuator coupled to the mouthpiece such that actuation of said mouthpiece actuator moves the mouthpiece towards said storage position and deactuation of the mouthpiece actuator moves the mouthpiece towards said in-use position,
wherein said body is shaped to be holdable in one hand and the mouthpiece actuator is actuable in response to a motion of the thumb on the same hand.

The motion of the thumb suitably, but not necessarily, involves contact, and typically engagement, of the thumb with the mouthpiece actuator resulting in the movement thereof.

In one preferred aspect, the body is shaped to be holdable in the palm of one hand.

In another preferred aspect, the body is shaped to be holdable in the palm and by at least one of the fingers of one hand.

In a further preferred aspect, the body is shaped to be holdable by a plurality of the fingers of one hand.

Preferably, the mouthpiece actuator is coupled to the mouthpiece such that movement of said mouthpiece actuator in a first direction moves the mouthpiece towards said storage position and movement of the mouthpiece actuator in an opposing direction moves the mouthpiece towards said in-use position.

Herein the term 'mouthpiece' is used in a generic sense to mean an element shaped such as to be insertable into the mouth or nose of a patient for inhalation therethrough.

In one preferred aspect, the mouthpiece actuator and mouthpiece are coupled by a coupling mechanism. In one particularly preferred aspect, the coupling mechanism comprises a rack and pinion mechanism. In another particularly preferred aspect, the coupling mechanism comprises a hinged lever mechanism.

In one aspect the medicament carrier is within the body. In another aspect the medicament carrier is attachable to the exterior of the body.

In another preferred aspect, the mouthpiece actuator and mouthpiece are directly coupled. Preferably the mouthpiece actuator is a rotatable turning device coupled to the mouthpiece. Alternatively a hinge mounting connects the mouthpiece to the body. Preferably the hinge mounting is sprung such as to bias the mouthpiece to the in-use position.

Preferably, the mouthpiece is comprised of an elastic material.

Preferably, the mouthpiece is provided with a cover comprised of an elastic material.

Preferably, the inhalation device additionally comprises a curtain arrangement contactable by the mouthpiece on movement of the mouthpiece from the storage to the in-use position. More preferably, the curtain arrangement comprises a plurality of curtains comprised of an elastomeric material.

Preferably, the mouthpiece actuator is provided with a safety trigger mechanism to prevent accidental actuation thereof.

Preferably, at least a portion of the mouthpiece actuator is shaped for ease of grip by the user.

Preferably, at least a portion of the mouthpiece actuator has a friction-enhancing coating.

Preferably, the device is provided with a dose counter, which indicates the number of doses dispensed from or remaining in the container. More preferably, the dose counter comprises an indexing mechanism actuated by a predetermined movement of the medicament container relative to the body.

Preferably, the medicament container is an aerosol or a dry-powder container.

According to another aspect of the present invention, there is provided the use of an inhalation device provided herein for dispensing medicament.

Preferred embodiments of the inhalation device according to the present invention will now be described with reference to the accompanying drawings in which:

FIG. 1a is a sectional side view of a first inhalation device in accord with the present invention, wherein the mouthpiece is in the storage position;

FIG. 1b is a sectional side view of the device of FIG. 1a, wherein the mouthpiece is in the in-use position;

FIG. 2a is a perspective view of a second inhalation device herein, wherein the mouthpiece is in the storage position;

FIG. 2b is a perspective view of the device of FIG. 2a, wherein the mouthpiece is in the in-use position;

FIG. 4a is a sectional side view of a fourth inhalation device herein, wherein the mouthpiece is in the storage position;

FIG. 4b is a sectional top view of the device of FIG. 4a; and

FIG. 4c is a sectional top view of the device of FIGS. 4a and 4b, wherein the mouthpiece is in the in-use position.

FIG. 6b is a sectional side view of the device of FIG. 6a;

FIG. 7a is a sectional plan view of a seventh inhalation device in accord with the present invention;

FIG. 7b is a sectional side view of the device of FIG. 7a wherein the mouthpiece is in the storage position;

FIG. 7c is a sectional side view of the device of FIG. 7a and FIG. 7b wherein the mouthpiece is in the in-use position.

Figure 3B:
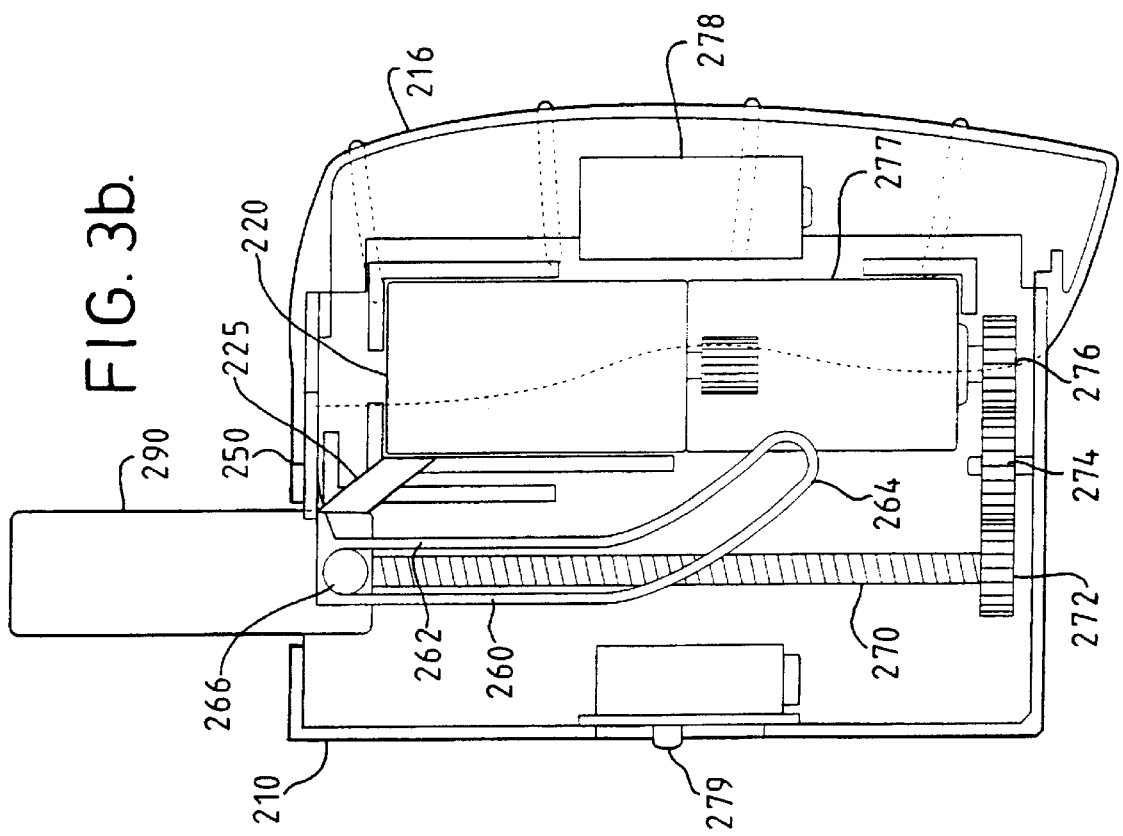
FIG. 3b is a sectional side view of the device of FIG. 3a, wherein the mouthpiece is in the in-use position.

FIGS. 1a and 1b shows a first inhalation device herein comprising a body 10 having an end cap 16, wherein the end cap 16 is reversibly attached to the body 10 by a snap fit mechanism 30,32. Within the body 10 there is provided a medicament container 20, and integral therewith a mouthpiece 90. In the storage position the mouthpiece 90 is kept protected from outside contamination by cover 50, which comprises an arrangement of elastomeric flaps 52, 54 forming a hygienic curtain. The integral medicament container 20 and mouthpiece 90 are mounted for translational movement on guide rails 60, 62. An outer face of the medicament container 20 is provided with a series of teeth forming a rack 70, which is in communication with first wheel 72 mounted for rotation on the body 10 thereby forming a rack and pinion mechanism. The first wheel 72 also communicates with second wheel 74, which is also mounted for rotation on the body 10. Rotation of the second wheel 74 is rotationally coupled to that of drive lever 76, which protrudes from the body 10 making it user accessible.

Actuation of the device from the storage position (shown in FIG. 1a) to the in-use position (shown in FIG. 1b) is achievable by a user-driven actuation of the drive lever 76. In practice, this can be achieved by a one-handed operation wherein the body 10 of the device is gripped between palm and fingers and the drive lever 76 is rotated by a motion of the thumb. It may be seen that rotation of the device lever 76 results in similar rotation of the second wheel 74 and opposite rotation of the first wheel 72, which engages with the rack 70 on the medicament container thereby driving the integral medicament container 20 and mouthpiece 90, upwardly along the guide rails 60, 62 to the in-use position. Ejection of the medicament container 20 from the body 10 is prevented by stops 64, 66.

It may also be seen that on actuation the mouthpiece 90 impacts with, and causes a parting, of the protective curtain arrangement 52, 54. In an improvement herein, the curtains 52, 54 may be provided with a friction cleaning surface or coating such that the mouthpiece is cleaned of any dust particles, dirt etc., when it contacts the curtains. Deactivation of the device is achievable by the reverse rotation of the drive lever 76.

FIGS. 2a and 2b show a second inhalation device herein having an actuation mechanism (not shown in detail) similar to that of the device of FIGS. 1a and 1b. The device comprises a body 110 having a reversibly removable end cap 116. Within the body there is provided an integral medicament cartridge (not visible) and mouthpiece 190. A protective cover 150 is provided to the end cap 116, wherein the cover 150 prevents ingress of dirt and contamination to the mouthpiece 190 within the body 110. The drive lever 76 of the device of FIGS. 1a and 1b is replaced by a rotationally mounted drive cylinder 176, which has a grooved surface for ease of grip. It may be appreciated that the body 110 is shaped for ease of grip within the palm of a user's hand and the drive cylinder 176 is arranged for ease of rotation by a thumb motion. Actuation of the device is achievable by rotation of the drive cylinder 176 towards the end cap 116 and deactivation is achievable by the reverse rotatory movement.

Figure 3A:
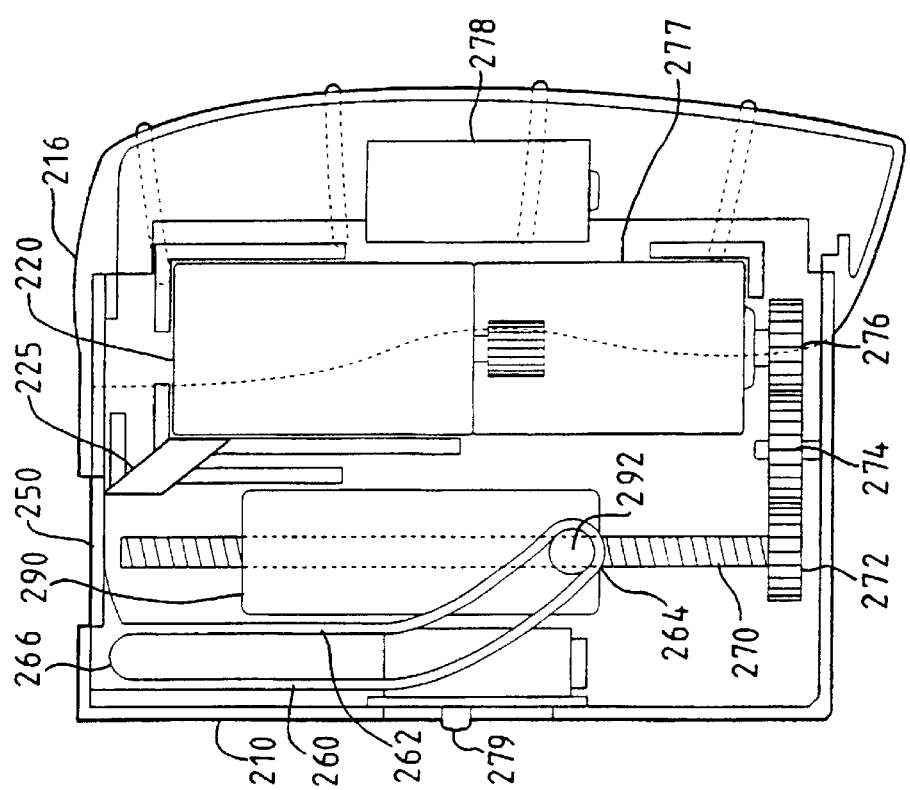
FIG. 3a is a sectional side view of a third inhalation device herein, wherein the mouthpiece is in the storage position.

FIGS. 3a and 3b shows a third inhalation device herein comprising a body 210 having a reversibly detachable side position 216, which is shaped for ease of grip. Within the body 210 there is provided a medicament container 220. Also provided is mouthpiece 290, which communicates with the medicament container through a connecting passage 225 when the mouthpiece is in the in-use position. The mouthpiece 290 is mounted on worm 270, such that the worm 270 is rotationally movable therewithin. The worm 270 is provided at the lower end with a worm drive wheel 272, which communicates with a second wheel 274 mounted on the body 210, which second wheel 274 communicates with a motor drive wheel 276. The motor drive wheel is driven by motor 277 powered by battery 278. A user accessible switch 279 is provided for actuation of the motor 278.

Rotation of the mouthpiece 290 is prevented by the presence of stub 292 on the mouthpiece 290. The stub 292, and hence mouthpiece 290, is mounted on movable guide rails 260, 262 having first and second end stops 264, 266 corresponding respectively to the mouthpiece storage and in-use positions. The upper end 266 of the movable guide rail arrangement 260, 262 is attached to a sliding door 250. The sliding door 250 is closed when the mouthpiece 290 is in the storage position thereby forming a protective cover. The door 250 is slidably openable in response to actuation of the mouthpiece 290, thereby allowing the mouthpiece 290 to protrude through the door opening.

Actuation of the device from the storage position (shown in FIG. 3a) to the in-use position (shown in FIG. 3b) is achievable by user actuation of the switch 279. It may be appreciated that the device as a whole is shaped for one-handed operation involving gripping of the end cap 216 by the fingers and thumb actuation of the switch 279. On actuation the motor 277 rotationally drives motor drive wheel 276, in turn causing rotation of the second wheel 274, worm drive wheel 272 and hence worm 270. The upward rotational movement of the worm 270 causes the mouthpiece 290 and stub 292 thereon to be driven upwards along a path defined by the axis of rotation of the worm 270.

Since the stub 292 is mounted on the guide rail arrangement 260, 262, it may be seen that the upwards movement of the stub 292 causes the shaped guide rails 260, 262 to be driven sideways (from left to right as shown), hence enabling opening of the sliding door 250, which is itself attached to the upper end 266 of the guide rail arrangement 260, 262.

Deactuation of the device is achievable by a second actuation actuation of the switch 279, which results in the opposite motor-driven rotation of the gear assembly 272, 274, 276 and worm drive 270.

FIGS. 4a, 4b and 4c show a fourth inhalation device herein comprising a disk-shaped body 310. At three equally spaced positions on the periphery of the disk-shaped body 310 there are provided actuation pads 360, 362, 364. The pads 360, 362, 364 are shaped for ease of grip by a user. Three equally spaced slits are also provided on the periphery of the body 310 for receipt of actuating pins 314, 316, 318 mounted on the interior of each pad 360, 362, 364, which pins 314, 316, 318 protrude into the body 310. Compression of an actuating pad 360, 362, 364 relative to the body 310 thus results in movement of a pin 314, 316, 318 into the slits, and hence its insertion deeper into the body 310. When so inserted, the pin 314, 316, 318 contacts generally disk-shaped plate 370, which is mounted for rotation within the body 310, causing rotation thereof. FIG. 4c shows a device in which pad 360 has been compressed moving pin 314 into the body 310 and into contact with plate 370, which has thus been rotated.

Within the body 310 there is provided a medicament container 320 and integral therewith a mouthpiece 390. The mouthpiece 390 is connected to the generally disk-shaped plate 370 by pivotally mounted arms. FIGS. 4a, thus shows arm 392 mounted to the plate 370 at pivot point 394, which arm is itself mounted to mouthpiece 390. The arm 392 contacts a triangular cam surface 396 provided on the body 310. When the plate 370 is rotated the contact of the arms 392 with the camming surface results in the arms 392, and hence the mouthpiece 390, being urged upwardly towards a circular opening 312 in the body. In the storage position the opening 312 is closed off by an iris shutter mechanism comprising three shaped doors 350, 352, 354 capable of forming a circular closure. Each of the doors 350, 352 354 is pivotally mounted to the generally disk-shaped plate 370 at pivot points 351, 353 and 355.

The iris closure is generally urged towards the closed position by leaf spring mechanisms 394, 396, 398. The rotation of the pate 370 relative to the body 310 may, thus, be seen to allow for opening and closing of the iris shutter mechanism. Rotation of the plate 370 is initiated by its drivable contact by one or more of the actuating pins 314, 316, 318.

A lock mechanism is further provided, which allows for reversable locking of the device in the 'in-use' (i.e. iris shutter open and mouthpiece protruding) position. The locking mechanism comprises locking arm 340 mounted at a first end at pivot point 342 to the body 310. The second end of the arm is provided with a stub 344, which is mounted for travel on irregular-shaped track 346 provided in the plate 370. As the plate 370 is rotated, the stub 344 moves along the track 346 until it is retainably received by valley 348 in the track 346, which corresponds to the locking position. Unlocking is achieved by further rotation of the plate 370, which allows for release of the stub 344 from the valley 348 in the track 346.

Actuation of the device from the storage position (shown in FIGS. 4a and 4b) to the in-use position (shown in FIG. 4c) is achievable by a user-driven compression of one or more of the actuating pads 360, 362, 364. It will be appreciated that such compressive force may be conveniently achieved by a user holding the body 310 of the device in a cupped hand and using the thumb to squeeze down one of the actuating pads 360, 362, 364. Compression of an actuating pad 360, 362, 364 results in an actuating pin 314, 316, 318 being pushed into the body 310 of the device. The actuating pin 314, 316, 318 contacts the plate 370 causing rotation thereof, which rotation in turn results in the opening of the iris shutter mechanism, and ejection of the mouthpiece 390 from the opening 312 thereby revealed in the body 310. The iris shutter and mouthpiece are locked into the 'in use' position by the hereinbefore described locking mechanism. Deactuation is achieved by application of further compressive force to an actuating pad 360, 362, 364 resulting in further insertion of a pin 314, 316, 318 which in turn further rotates the plate 370, and, thus, results in unlocking of the lock mechanism. The plate 370 may then rotate back to its start position under the influence of the spring mechanism 394, 396, 398 which also causes closing of the iris shutter.

Figure 5A:
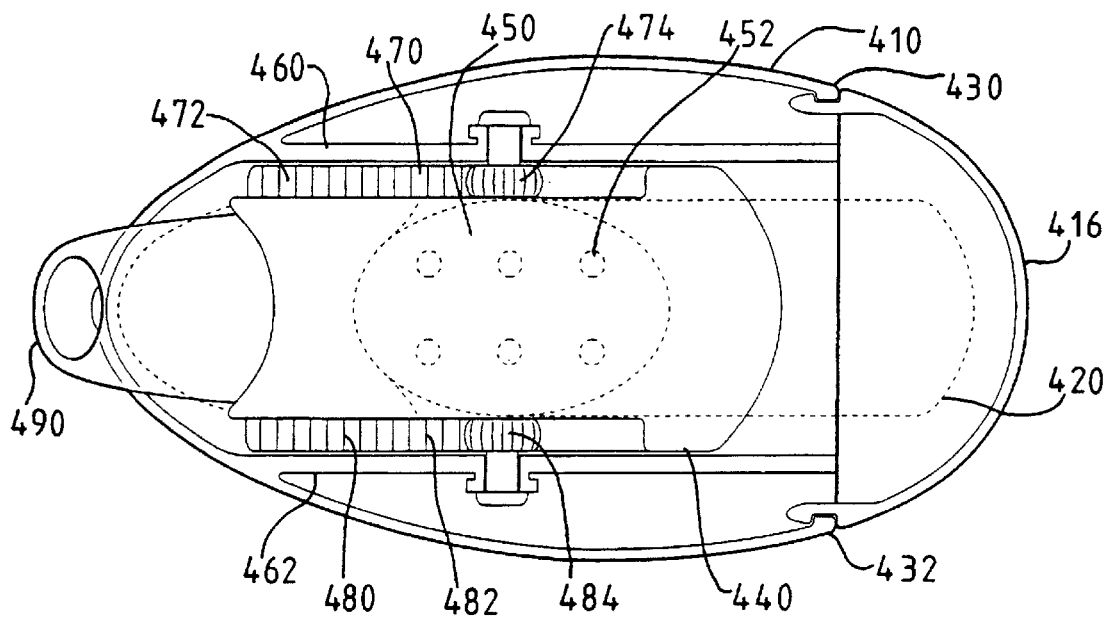
FIG. 5a is a sectional plan view of a fifth inhalation device in accord with the present invention.
Figure 5B:
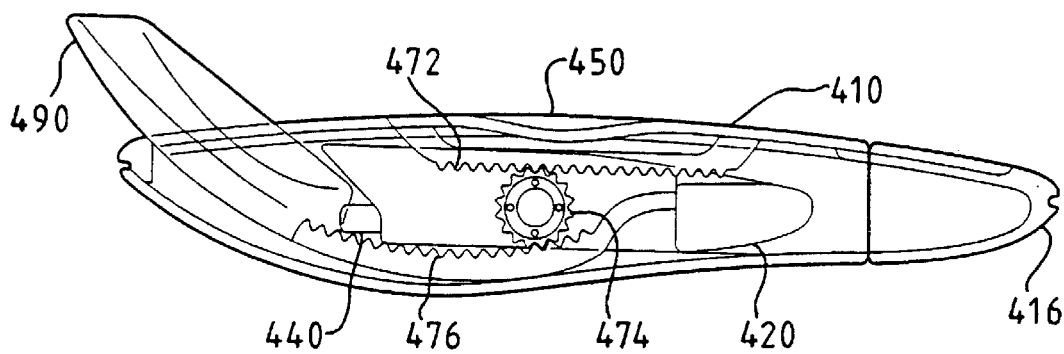
FIG. 5b is a sectional side view of the device of FIG. 5a, wherein the mouthpiece is in the in-use position.
Figure 5C:
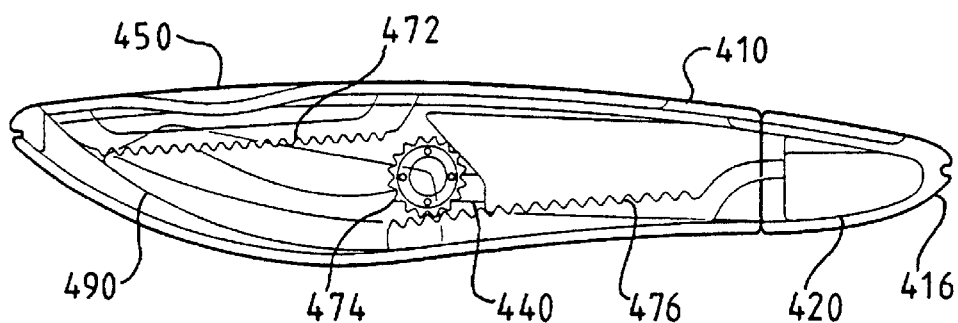
FIG. 5c is a sectional side view of the device of FIG. 5a, wherein the mouthpiece is in the storage position.

FIGS. 5a, 5b and 5c show a first inhalation device herein comprising a body 410 having an end cap 416, wherein the end cap 416 is reversibly attached to the body 410 by a snap fit mechanism 430, 432. Within the body there is provided a medicament container 420, which is in communication with a hollow transition piece 440 also provided in said body 410.

An essentially flat cover 450 is retainably mounted on first and second guide rails 460, 462 provided on a first face of the body 410 for slidable movement thereon. The exterior surface of the cover 450 has contours 452 for ease of grip by the thumb of the user. The interior surface of the cover 450 communicates with first and second rack pinion mechanisms 470, 480 which are aligned with the axes defined by the first and second guide rails 460, 462. Each of the first and second rack and pinion mechanisms 470, 480 (wherein, for clarity, only the first mechanism is shown in detail on FIGS. 5b and 5c) comprises a first rack 472, 482 attached to the cover 450, which communicates with a wheel 474, 484 axially mounted to the body 410, which wheel 474, 484 communicates with a curved second rack 476 which is mounted for communication with the mouthpiece 490.

Actuation of the device from the storage position (shown in 5c) to the in-use position) (shown in FIGS. 5a and 5c) is achievable by the user holding the body 410 in a cupped palm and using a thumb motion to slide the cover 450 along the guide rails 460, 462 in a direction towards the end cap 416. The first rack 472 is thus bought into engagement with wheel 474, which rotates and engages second rack 476, thereby moving the second rack 476 in the opposite direction. In turn, the movement of the second rack 476 causes the mouthpiece 490 to be moved to the in-use position, in which it protrudes from the body 410. In the in-use position it may be seen that the interior of the mouthpiece 490 communicates with the hollow interior of the transition piece 440, which itself communicates with the medicament container 420. Thus an inhalation passageway is provided from the mouthpiece 490 to the medicament container 420. Deactivation is achievable by the reverse sliding motion of the cover 450.

Figure 6B:
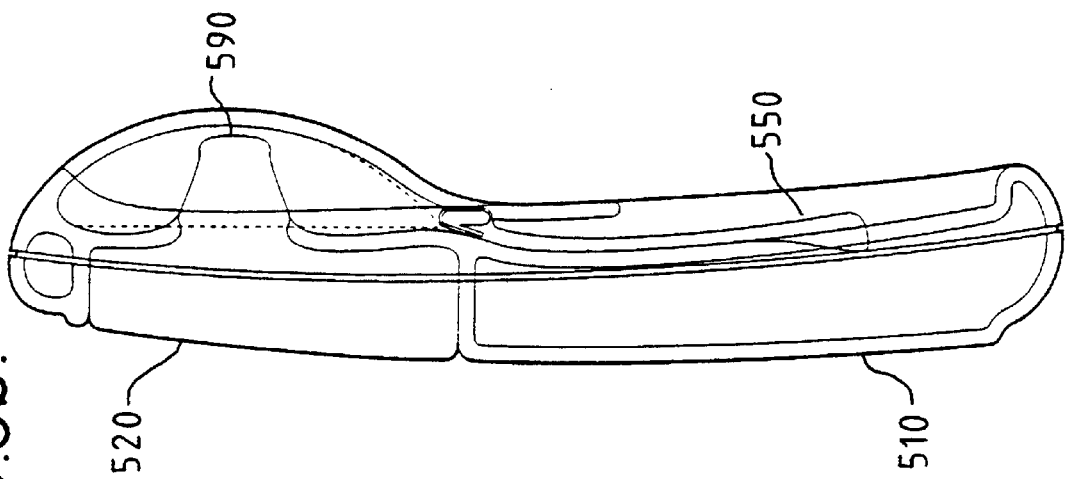
Figure 6A:
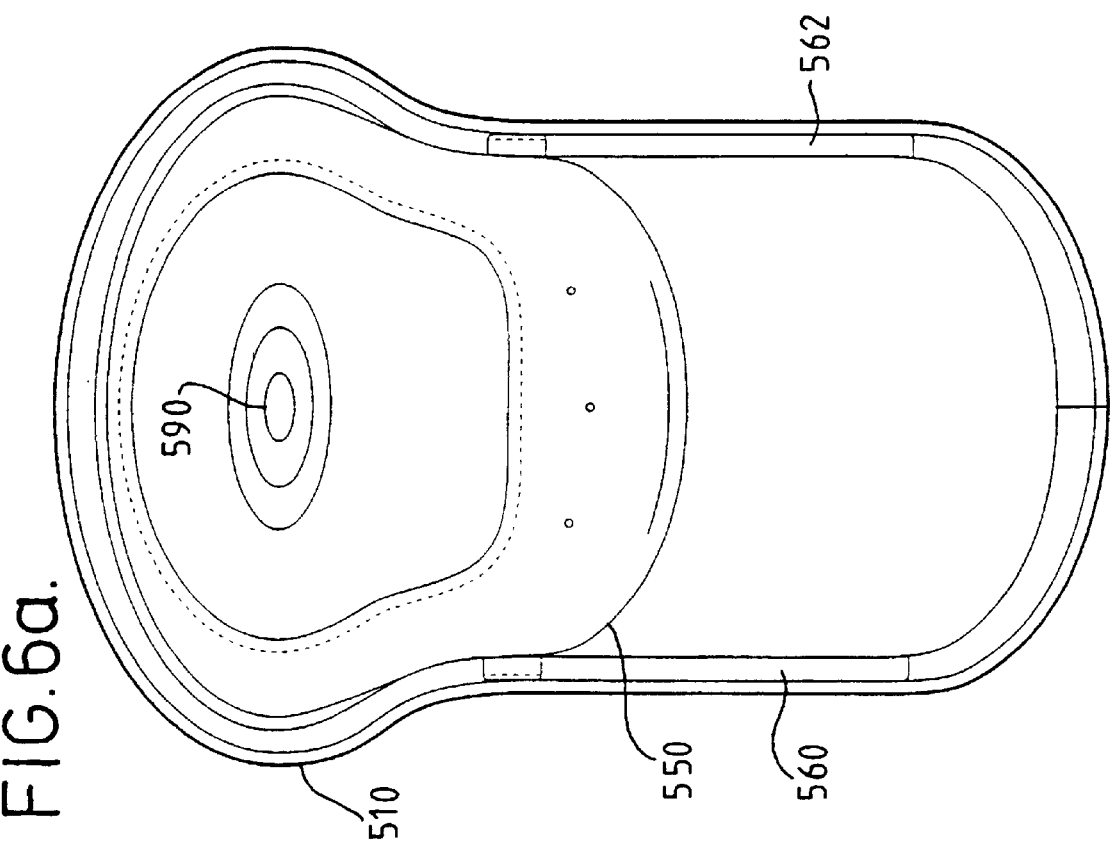
FIG. 6a is a sectional plan view of a sixth inhalation device in accord with the present invention.

FIGS. 6a and 6b shows a sixth inhalation device herein comprising a body 510, which is overall shaped for ease of grip in the hand of a user. Within the body 510 there is provided a medicament cartridge 520 and attached thereto mouthpiece 590, wherein the mouthpiece is comprised of a resiliently deformable elastomeric material. A shaped cover 550 is retainably mounted on first and second guide rails 560, 562 provided on the body 510 for slidable movement thereon.

Actuation of the device from the storage position (shown in FIG. 6a) to the in-use position (shown in FIG. 6b) is achievable by the user gripping the body 510 of the device in a partially cupped palm and using the thumb to slide the cover 550 along the guide rails 560, 562, thereby revealing the mouthpiece 590, which 'pops out' into its characteristic shape. Deactivation is achievable by the reverse sliding action, which causes deformation of the mouthpiece 590.

FIGS. 7a, 7b and 7c show a seventh inhalation device herein comprising a body 610 provided with a medicament compartment 620 which is accessible for loading of medicament by opening of door 622. Contoured elastomeric strips 616, 618 are provided to the body 610 for ease of grip thereof by the hand of a user.

A circular, essentially flat cover 650 is retainably mounted on the first and second guide rails 660, 662 provided on the body 610. The interior surface of the cover 650 is coupled through articulated assembly 670 to mouthpiece 690, which is itself hingedly mounted. The mouthpiece 690 is provided with a thin, flexible elastomeric covering 692.

Actuation of the device from the storage position (shown in FIGS. 7a and 7b) to the in-use position (shown in FIG. 7c) is achievable by the user holding the body 610 of the device in one hand and using the thumb to slidably move the cover 650 along the guide rails 660, 662. The sliding action is coupled via articulated assembly 670 to the mouthpiece 690, which is moved to a position in which it stands proud from the body 610, and in which there is an inhalation passageway established between the mouthpiece 690 and the medicament compartment 620. Deactivation is achievable by performance of the reverse sliding action.

Figure 8B:
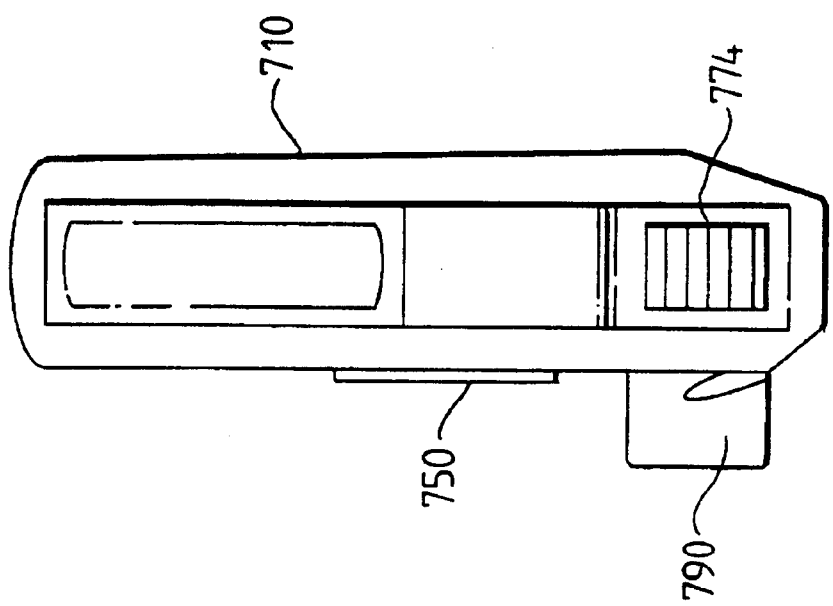
FIG. 8b is a side view of the device of FIG. 8a wherein the mouthpiece is in the in-use position.
Figure 8A:
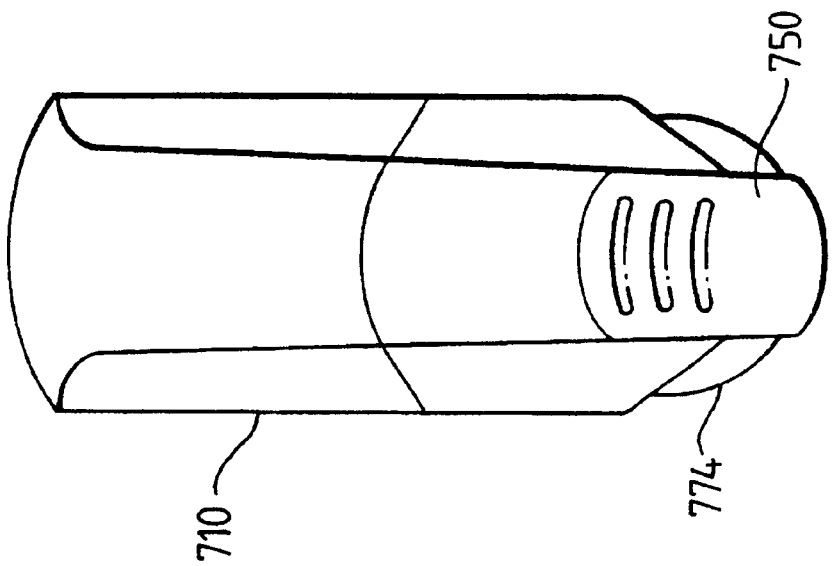
FIG. 8a is a front view of an eighth inhalation device in accord with the present invention.

FIGS. 8a and 8b show an inhalation device herein comprising a body 710, within said body 710 there is provided a hidden mouthpiece 790 and a medicament cartridge (not visible). A protective cover 750 of the mouthpiece 790 is provided which prevents ingress of dirt and contamination to the mouthpiece 790 within the body 710. The protective cover 750 is reversibly slidable to expose or cover hidden retracted mouthpiece 790.

There is provided a rotationally mounted drive cylinder 774, which has a grooved surface for ease of grip. It may be appreciated that the body 710 is shaped for ease of grip within the palm of a user's hand and the drive cylinder 774 is arranged for ease of rotation by a thumb motion. Actuation of the mouthpiece 790 is achievable by rotation of the drive cylinder 774 and deactuation is achievable by the reverse rotary movement.

Figure 9C:
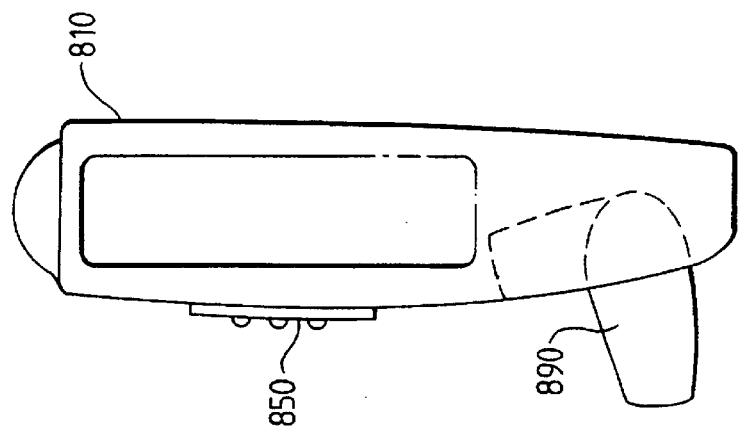
FIG. 9c is a side view of the device of FIG. 9b wherein the mouthpiece is in the in-use position.
Figure 9B:
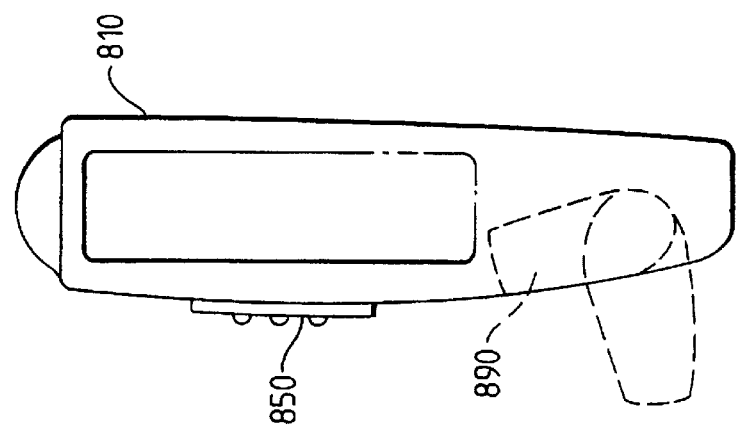
FIG. 9b is a side view of the device of FIG. 9a wherein the mouthpiece is in the storage position.
Figure 9A:
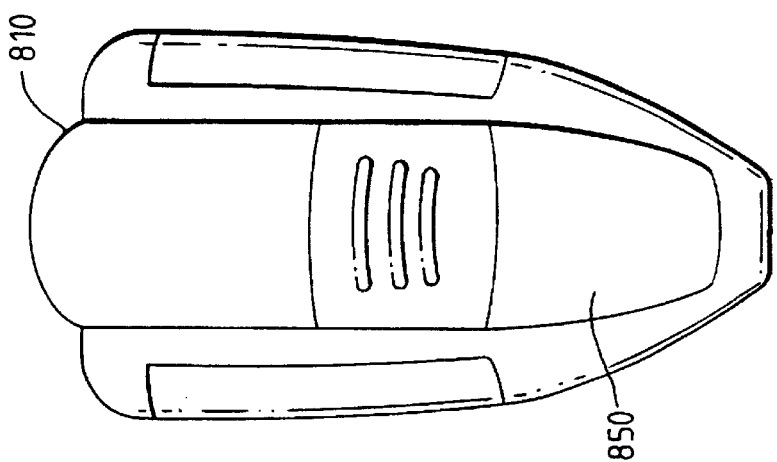
FIG. 9a is a front view of a ninth inhalation device in accord with the present invention.

FIGS. 9a, 9b and 9c show an inhalation device herein comprising a body 810, within said body there is provided a hidden mouthpiece 890 and a medicament cartridge (not visible). A protective cover 850 of the mouthpiece 890 is provided which prevents ingress of dirt and contamination to the mouthpiece 890 within the body 810. The protective cover 850 is reversibly slidable to expose or cover hidden retracted mouthpiece 890. There is provided a spring mounted hinge (not visible) on the mouthpiece 890, which allows the mouthpiece 890 to spring into the in-use position following movement of the protective mouthpiece cover 850 to expose the stored mouthpiece 890.

The body 810 of the inhalation device is shaped to fit within the user's hand. Actuation of the device from the storage position to the in-use position is achievable by using the thumb of the same hand to slidably move the protective mouthpiece cover 850, allowing the hinged mouthpiece 890 to move into the in-use position. Deactuation of the mouthpiece is achievable by using the thumb to move the mouthpiece 890 back to the storage position and to slide the protective mouthpiece cover 850 so that it covers the mouthpiece 890 again.

The inhalation device herein is suitable for dispensing medicament, particularly for the treatment of respiratory disorders. Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate, ketotifen or nedocromil; antiinfectives e.g., cephalosporins, penicillins, streptomycin, sulphonamides, tetracyclines and pentamidine; antihistamines, e.g., methapyrilene; anti- inflammatories, e.g., beclomethasone dipropionate, fluticasone propionate, flunisolide, budesonide, rofleponide, mometasone furoate or triamcinolone acetonide; antitussives, e.g., noscapine; bronchodilators, e.g., albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, or (−)-4-amino-3,5-dichloro-α-[[[6-[2-(2- pyridinyl)ethoxy]hexyl]methyl] benzenemethanol; diuretics, e.g., amiloride; anticholinergics, e.g., ipratropium, tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are selected from albuterol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) in combination with an anti-inflammatory steroid such as a beclomethasone ester (e.g., the dipropionate) or a fluticasone ester (e.g., the propionate).

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

What is claimed is:

1. An inhalation device for dispensing medicament comprising
    a body;
    a medicament carrier;
    a mouthpiece, reversibly movable from a storage position wherein said mouthpiece is within said body to an in-use position wherein a portion of the mouthpiece protrudes from the body and wherein the mouthpiece is in communication with said medicament carrier to allow passage of medicament therebetween; and
    a mouthpiece actuator coupled to the mouthpiece such that actuation of said mouthpiece actuator moves the mouthpiece towards said storage position and deactuation of the mouthpiece actuator moves the mouthpiece towards said in-use position,
wherein said body is shaped to be holdable in one hand and the mouthpiece actuator is actuable in response to a discrete motion of the thumb on the same hand, and the mouthpiece actuator and mouthpiece are directly coupled.

2. An inhalation device according to claim 1 wherein the mouthpiece actuator is a rotatable turning device coupled to the mouthpiece.

3. Use of an inhalation device according to claim 1 for dispensing medicament.

4. An inhalation device for dispensing medicament comprising
    a body;
    a medicament carrier;
    a mouthpiece, reversibly movable from a storage position wherein said mouthpiece is within said body to an in-use position wherein a portion of the mouthpiece protrudes from the body and wherein the mouthpiece is in communication with said medicament carrier to allow passage of medicament therebetween; and
    a mouthpiece actuator coupled to the mouthpiece such that actuation of said mouthpiece actuator moves the mouthpiece towards said storage position and deactuation of the mouthpiece actuator moves the mouthpiece towards said in-use position,
wherein said body is shaped to be holdable in one hand and the mouthpiece actuator is actuable in response to a discrete motion of the thumb on the same hand, and the medicament carrier is attachable to the exterior of the body.

5. An inhalation device according to claim 4, wherein the mouthpiece is comprised of an elastic material.

6. An inhalation device according to claim 4, wherein the mouthpiece is provided with a cover comprised of an elastic material.

7. An inhalation device according to claim 4, wherein at least a portion of the mouthpiece actuator is shaped for ease of grip by the user.

8. Use of an inhalation device according to claim 4 for dispensing medicament.

9. An inhalation device for dispensing medicament comprising
    a body;
    a medicament carrier;
    a mouthpiece, reversibly movable from a storage position wherein said mouthpiece is within said body to an in-use position wherein a portion of the mouthpiece protrudes from the body and wherein the mouthpiece is in communication with said medicament carrier to allow passage of medicament therebetween; and
    a mouthpiece actuator coupled to the mouthpiece such that actuation of said mouthpiece actuator moves the mouthpiece towards said storage position and deactuation of the mouthpiece actuator moves the mouthpiece towards said in-use position,
wherein said body is shaped to be holdable in one hand and the mouthpiece actuator is actuable in response to a discrete motion of the thumb on the same hand, and additionally comprising a curtain arrangement contactable by the mouthpiece on movement of the mouthpiece from the storage to the in-use position.

10. An inhalation device according to claim 9, wherein said curtain arrangement comprises a plurality of curtains comprised of an elastomeric material.

11. An inhalation device according to claim 9, wherein the medicament container is an aerosol.

12. Use of an inhalation device according to claim 9 for dispensing medicament.

13. An inhalation device for dispensing medicament comprising
    a body;
    a medicament carrier;
    a mouthpiece, reversibly movable from a storage position wherein said mouthpiece is within said body to an in-use position wherein a portion of the mouthpiece protrudes from the body and wherein the mouthpiece is in communication with said medicament carrier to allow passage of medicament therebetween; and
    a mouthpiece actuator coupled to the mouthpiece such that actuation of said mouthpiece actuator moves the mouthpiece towards said storage position and deactuation of the mouthpiece actuator moves the mouthpiece towards said in-use position,
wherein said body is shaped to be holdable in one hand and the mouthpiece actuator is actuable in response to a discrete motion of the thumb on the same hand, and the mouthpiece actuator is provided with a safety trigger mechanism to prevent accidental actuation thereof.

14. Use of an inhalation device according to claim 13 for dispensing medicament.

15. An inhalation device for dispensing medicament comprising a body;

a medicament carrier;

a mouthpiece, reversibly movable from a storage position wherein said mouthpiece is within said body to an in-use position wherein a portion of the mouthpiece protrudes from the body and wherein the mouthpiece is in communication with said medicament carrier to allow passage of medicament therebetween; and a mouthpiece actuator coupled to the mouthpiece such that actuation of said mouthpiece actuator moves the mouthpiece towards said storage position and deactuation of the mouthpiece actuator moves the mouthpiece towards said in-use position, wherein said body is shaped to be holdable in one hand and the mouthpiece actuator is actuable in response to a discrete motion of the thumb on the same hand, and at least a portion of the mouthpiece actuator has a friction-enhancing coating.

16. Use of an inhalation device according to claim 15 for dispensing medicament.

17. An inhalation device for dispensing medicament comprising a body;

a medicament carrier;

a mouthpiece, reversibly movable from a storage position wherein said mouthpiece is within said body to an in-use position wherein a portion of the mouthpiece protrudes from the body and wherein the mouthpiece is in communication with said medicament carrier to allow passage of medicament therebetween; and a mouthpiece actuator coupled to the mouthpiece such that actuation of said mouthpiece actuator moves the mouthpiece towards said storage position and deactuation of the mouthpiece actuator moves the mouthpiece towards said in-use position, wherein said body is shaped to be holdable in one hand and the mouthpiece actuator is actuable in response to a discrete motion of the thumb on the same hand, and the medicament container is a dry-powder container.

18. Use of an inhalation device according to claim 17 for dispensing medicament.

19. An inhalation device for dispensing medicament comprising a body;

a medicament carrier;

a mouthpiece, reversibly movable from a storage position wherein said mouthpiece is within said body to an in-use position wherein a portion of the mouthpiece protrudes from the body and wherein the mouthpiece is in communication with said medicament carrier to allow passage of medicament therebetween; and a mouthpiece actuator coupled to the mouthpiece such that actuation of said mouthpiece actuator moves the mouthpiece towards said storage position and deactuation of the mouthpiece actuator moves the mouthpiece towards said in-use position, wherein said body is shaped to be holdable in one hand and the mouthpiece actuator is actuable in response to a discrete motion of the thumb on the same hand, and the device is provided with a dose counter.

20. An inhalation device according to claim 19 wherein the dose counter comprises an indexing mechanism actuated by a predetermined movement of the medicament container relative to the body.

21. Use of an inhalation device according to claim 19 for dispensing medicament.

* * * * *

UNITED STATES PATENT AND TRADEMARK OFFICE
CERTIFICATE OF CORRECTION

PATENT NO. : 6,568,389 B1
DATED : May 27, 2003
INVENTOR(S) : Paul Kenneth Rand and Gregor John McLennan Anderson It is certified that error appears in the above-identified patent and that said Letters Patent is hereby corrected as shown below:

<u>Title page,</u>
Item [74], *Attorney, Agent or Firm,* delete "James F. Risk" insert -- James P. Riek --

Signed and Sealed this

Thirtieth Day of December, 2003

JAMES E. ROGAN
*Director of the United States Patent and Trademark Office*